United States Patent [19]

Dorenkott et al.

[11] Patent Number: 5,750,881
[45] Date of Patent: May 12, 1998

[54] METHOD AND APPARATUS FOR ASPIRATING AND DISPENSING SAMPLE FLUIDS

[75] Inventors: Jeffrey S. Dorenkott, North Olmsted; Steven E. Wilder, Ashland, both of Ohio; Dinh Nyugen, Liverpool, N.Y.; Kurukundi Ramesh Murthy, Fairview Park, Ohio

[73] Assignee: Chiron Diagnostics Corporation, E. Walpole, Mass.

[21] Appl. No.: 501,806

[22] Filed: Jul. 13, 1995

[51] Int. Cl.$^6$ .............................. G01M 3/02; B01L 3/02; G01N 1/14
[52] U.S. Cl. .................. 73/37; 73/864.11; 73/864.15; 422/100
[58] Field of Search ................ 73/863.01, 863.02, 73/864.11, 864.12, 864.15, 864.22, 37; 422/100

[56] References Cited

U.S. PATENT DOCUMENTS

| | | | |
|---|---|---|---|
| 3,912,456 | 10/1975 | Young | 23/253 |
| 4,004,862 | 1/1977 | Hill | 417/234 |
| 4,058,367 | 11/1977 | Gilford | 23/253 R |
| 4,091,671 | 5/1978 | McLees | 73/313 |
| 4,161,188 | 7/1979 | Jorgensen | 137/386 |
| 4,228,831 | 10/1980 | Kerns | 141/27 |
| 4,267,861 | 5/1981 | Roth | 137/625.48 |
| 4,296,373 | 10/1981 | Angel et al. | 324/71 CP |
| 4,417,472 | 11/1983 | Tward | 73/304 |
| 4,431,606 | 2/1984 | Revillet et al. | 422/102 |
| 4,477,578 | 10/1984 | Miles et al. | 435/518 |
| 4,522,228 | 6/1985 | Campau | 137/393 |
| 4,525,850 | 7/1985 | Miller | 377/19 |
| 4,731,225 | 3/1988 | Wakatake | 422/65 |
| 4,774,057 | 9/1988 | Uffenheimer et al. | 422/100 |
| 4,780,833 | 10/1988 | Atake | 364/509 |
| 4,790,183 | 12/1988 | Pfost et al. | 73/290 |
| 4,795,448 | 1/1989 | Stacey et al. | 604/319 |
| 4,818,493 | 4/1989 | Coville et al. | 422/102 |
| 4,818,706 | 4/1989 | Starr | 436/180 |
| 4,824,641 | 4/1989 | Williams | 422/100 |
| 4,843,883 | 7/1989 | Glover et al. | 73/301 |
| 4,878,383 | 11/1989 | Wiegand, Jr. et al. | 73/293 |

(List continued on next page.)

FOREIGN PATENT DOCUMENTS

| | | |
|---|---|---|
| 0163826 | 12/1985 | European Pat. Off. |
| 0223751 | 11/1986 | European Pat. Off. |
| 163821 | 6/1988 | European Pat. Off. |
| 0341438 | 11/1988 | European Pat. Off. |
| 0409606 | 1/1991 | European Pat. Off. |
| 0437906 | 7/1991 | European Pat. Off. |
| 0608423 | 4/1993 | European Pat. Off. |
| 0608425 | 4/1993 | European Pat. Off. |
| 0571100 | 11/1993 | European Pat. Off. |
| 0620421 | 10/1994 | European Pat. Off. |
| 3614954 | 11/1987 | Germany . |
| 4227338 | 2/1994 | Germany . |
| 4339933 | 6/1994 | Germany . |
| 80061 | 3/1993 | Japan . |
| 08545 | 5/1992 | WIPO . |
| 06020 | 3/1994 | WIPO . |
| 95/00829 | 1/1995 | WIPO . |

OTHER PUBLICATIONS

Omar S. Khalil et al., *Abbott Prism: a Multichannel Heterogeneous Chemiluminescence Immunoassay Analyzer*, Clinical Chemistry, vol. 37, No. 9, 1991, pp. 1540–1547.

*Primary Examiner*—Hezron E. Williams
*Assistant Examiner*—Daniel S. Larkin
*Attorney, Agent, or Firm*—Arthur S. Morgenstern; Gordon R. Moriarty; Robert P. Blackburn

[57] ABSTRACT

A method and apparatus for aspirating and dispensing a sample fluid. The apparatus includes an air source having an output port coupled to a first port of a flow through pressure transducer. A second port of the flow through pressure transducer is coupled to a first port of a sample probe. The flow through pressure transducer provides transducer signals to a detector circuit. In response to the transducer signals provided thereto, the detector detects the occurrence or non-occurrence of a plurality of different events.

13 Claims, 4 Drawing Sheets

U.S. PATENT DOCUMENTS

| | | | |
|---|---|---|---|
| 4,912,976 | 4/1990 | Labriola, II | 73/290 R |
| 4,920,797 | 5/1990 | Swartz et al. | 73/309 |
| 4,925,629 | 5/1990 | Schramm | 422/82.05 |
| 4,926,701 | 5/1990 | Tompkins | 73/864.15 |
| 4,944,922 | 7/1990 | Hayashi | 422/100 |
| 4,964,090 | 10/1990 | McCarthy | 367/162 |
| 4,970,468 | 11/1990 | Ishizawa et al. | 324/662 |
| 4,977,786 | 12/1990 | Davis | 73/864 |
| 5,000,044 | 3/1991 | Duffy et al. | 73/317 |
| 5,001,596 | 3/1991 | Hart | 361/284 |
| 5,013,529 | 5/1991 | Itoh | 422/100 |
| 5,015,322 | 5/1991 | Griffin et al. | 156/345 |
| 5,027,075 | 6/1991 | Harding, Jr. | 324/662 |
| 5,031,452 | 7/1991 | Dobson et al. | 73/304 R |
| 5,039,279 | 8/1991 | Natwick et al. | 417/63 |
| 5,042,299 | 8/1991 | Wells | 324/663 |
| 5,043,141 | 8/1991 | Wilson et al. | 422/52 |
| 5,082,628 | 1/1992 | Andreotti et al. | 422/82.08 |
| 5,094,260 | 3/1992 | Stuart et al. | 137/102 |
| 5,096,670 | 3/1992 | Harris et al. | 422/65 |
| 5,101,673 | 4/1992 | Uffenheimer et al. | 73/864.22 |
| 5,111,703 | 5/1992 | Allen | 73/864.11 |
| 5,133,218 | 7/1992 | Uffenhiemer et al. | 73/864 |
| 5,143,849 | 9/1992 | Barry et al. | 436/50 |
| 5,146,783 | 9/1992 | Jansche et al. | 73/301 |
| 5,160,714 | 11/1992 | Hardison | 423/220 |
| 5,163,324 | 11/1992 | Stewart | 73/302 |
| 5,185,002 | 2/1993 | Venturini | 604/30 |
| 5,186,172 | 2/1993 | Fiddian-Green | 128/632 |
| 5,195,873 | 3/1993 | Claussen et al. | 417/18 |
| 5,211,678 | 5/1993 | Stephenson et al. | 73/149 |
| 5,215,714 | 6/1993 | Okada et al. | 422/64 |
| 5,242,404 | 9/1993 | Conley et al. | 604/119 |
| 5,245,292 | 9/1993 | Milesky et al. | 324/639 |
| 5,245,869 | 9/1993 | Clarke et al. | 73/149 |
| 5,271,897 | 12/1993 | Wurschum et al. | 422/63 |
| 5,271,902 | 12/1993 | Sakka et al. | 422/100 |
| 5,272,920 | 12/1993 | Stephenson | 73/301 |
| 5,272,921 | 12/1993 | Föller et al. | 73/304 |
| 5,275,951 | 1/1994 | Chow et al. | 435/50 |
| 5,315,867 | 5/1994 | Härtel et al. | 73/149 |
| 5,319,964 | 6/1994 | Stephenson et al. | 73/149 |
| 5,506,142 | 4/1996 | Mahaffey et al. | 422/100 X |
| 5,540,081 | 7/1996 | Takeda et al. | 73/37 |

METHOD AND APPARATUS FOR ASPIRATING AND DISPENSING SAMPLE FLUIDS

FIELD OF THE INVENTION

The invention relates to the field of automated fluid sample devices and more particularly, to apparatus for detecting when a sample probe of an automated fluid sample system contacts a liquid.

BACKGROUND OF THE INVENTION

As is known in the art, automated analyzers are used in clinical laboratories to measure the various chemical constituents of body fluids, such as whole blood, blood serum, blood plasma, cerebral spinal fluid, urine, and the like obtained from patients. Automated analyzers reduce the number of trained technicians required to perform the analyses in a clinical laboratory, improve the accuracy of the testing and reduce the cost per test.

Typically, an automated analyzer includes an automated fluid moving system which automatically aspirates a sample of body fluid from a patient's specimen container and dispenses the sample into a reaction cuvette. The fluid moving system typically includes a pipette which accomplishes the aspirate and dispensing functions under the control of a robotic arm.

Chemical reagents, which are specific to the test being performed, are disposed into the sample-containing cuvette thereby mixing the sample with the chemical reagents. By examining the reaction products resulting from the mixing of the sample and reagents, the automated analyzer determines the concentration of the specific chemical constituent, for which the testing is being performed, in the patient's specimen. Upon completion of the test, the automated analyzer typically prints the results of the test, including a sample identifier, a numerical result of the test, and a range of values for the chemical constituent as measured by the test.

During an aspiration operation, the robotic arm, under command of a system controller, positions the pipette above a specimen container and moves the pipette into the container until the pipette reaches the fluid in the container. A syringe type pump is then typically operated to draw sample fluid from the specimen container into the pipette.

One problem that occurs with the fluid moving systems is that occasionally upon aspirating a sample, the sample pipette fails to be properly disposed in the sample to be aspirated. In this case air, rather than a patient specimen, is drawn into the pipette. This prevents the necessary sample volume of the fluid specimen from being aspirated or from being completely dispensed into the reaction cuvette. If an improper sample volume of specimen is mixed with the reagents, an incorrect test result will typically be obtained.

Generally, when a clinician obtains an unusual test result, the test is repeated and the new result compared to the previous result. If the two results do not agree to within a predetermined limit, the test must be repeated a second time in order to determine which of the previous two results is valid.

Thus, it would be desirable to provide an automated fluid sample aspiration/dispensation device which detects physical contact between a probe tip and a surface of a liquid to thus ensure that a fluid rather than air is drawn in to the sample probe.

SUMMARY OF THE INVENTION

In accordance with the present invention, an apparatus for aspirating and dispensing a sample fluid includes an air source having an output port coupled to an input port of a flow through pressure transducer. An output of the flow through pressure transducer is coupled to a sample probe which has a tip that contacts the sample fluid. With this particular arrangement an apparatus for detecting physical contact between the sample probe and a surface of a liquid sample is provided. The pressure transducer senses pressure changes which result from a number of other events including but not limited to: (a) fluid leaks in a fluid path; (b) aspiration through the sample probe; (c) obstruction of a sample probe tip; and (d) attachment and detachment of a sample tip to a sample probe. The apparatus may also include a detector circuit coupled to the transducer. In response to each of the above-identified events, the flow through pressure transducer provides a differential voltage signal to the detector circuit.

In a surface detection mode of operation the air source provides a constant air flow through the pressure transducer and the sample probe, and probe tip while the sample probe is being lowered toward a surface of a fluid. Once the sample probe tip reaches the surface of the liquid, the pressure transducer senses a change in pressure of the air path in which the pressure transducer is disposed. In response to the pressure change the transducer provides transducer signals to the detector circuit. The detector circuit detects the signals provided thereto and provides a control signal to a system controller.

The detector circuit may be provided with the capability to detect several events including but not limited to: leaks; fluid level; aspirate integrity; clots; tip presence and pump servo integrity. Each of the events result in identifying signals being provided to a system controller for control of the air pump and the sample probe.

In detecting the position of a surface of a fluid, a sample probe is moved toward a fluid surface and when contact is made, a change in pressure in the air path inline with the flow through pressure transducer provides a pressure transducer signal representative of the contact, further permitting determination and the location of the fluid surface.

Leaks in a fluid path of an aspirate and dispense apparatus uses the same apparatus operated to occlude the sample probe tip by inserting the sample probe tip into a sample fluid and sensing the signal provided by the pressure transducer. A sensed pressure below a normalized pressure indicates leaks in the fluid path of the aspirate and dispense apparatus. If a leak exists the pressure will not rise to the normal level each time. The normal pressure can be established by placing a calibration tip having no opening for aspiration onto the sample probe body.

The detector circuit also detects when a sample probe tip is being coupled to a sample probe at a tip loader and removal of the sample probe tip at a tip dispense position by the increase in pressure when the smaller tip opening is placed over the sample probe. The detector circuit also detects when a sample probe tip is occluded by an obstruction during an aspirate or dispense operation. The occlusion must be severe enough to trigger a predetermined pressure change in the pressure transducer. The detector circuit also provides an indication whether a system bleed valve is closed or open. The detector circuit also evaluates the pump servo integrity by comparing the voltage on the air pump voltage with a voltage of the pressure transducer in the tubing and determining whether the voltage relationship is within predetermined limits. The detector circuit also determines aspirate integrity by verifying that an air aspiration results in a pressure change within predetermined limits.

BRIEF DESCRIPTION OF THE DRAWINGS

This invention is pointed out with particularity in the appended claims. The above and further advantages of this invention may be better understood by referring to the following description taken in conjunction with the accompanying drawing, in which:

Referring now to FIG. 1, aspirating and dispensing apparatus includes a constant air source 12 having an output port 12a coupled through a two way bleed valve 14 to a first port 16a of a three way pump valve 16. Bleed valve 14 has a vent 14' which is controlled by bleed valve 14 to be open or closed as described below.

Figure 1:
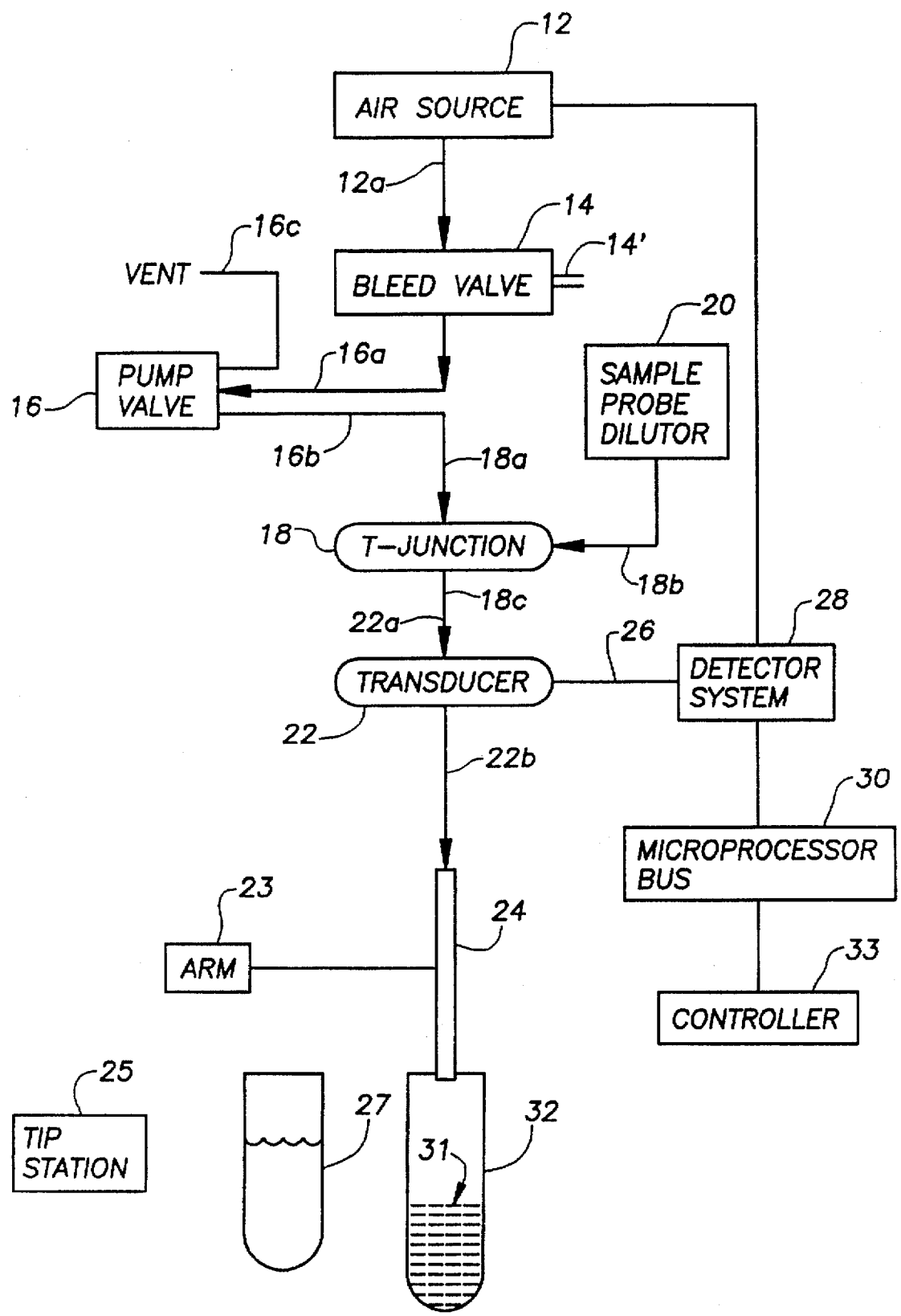
FIG. 1 is a block diagram of an automated fluid sample aspiration/dispensation apparatus.

The constant air source 12 should be of a type capable of providing a constant air flow at a predetermined rate and pressure to the pump valve 16. This rate and pressure is fairly low and depends on overall system parameters.

A second port 16b of pump valve 16 is coupled to a first input port 18a of a T-junction 18 and a third port 16c of the valve 16 is coupled to a vent. A second port 18b of the T-junction connector 18 is coupled to a sample probe diluter 20 which may be provided for example as a syringe or pumped diluter source.

A third port 18c of T-junction connector 18 is coupled to a flow through pressure transducer 22 at a first port 22a. A second port 22b of the transducer 22 is coupled to a sample probe 24 which may, for example, be provided as a pipette tube holder. Thus the pressure transducer 22 is located in-line with a fluid conduit between the air source 12 and the sample probe 24.

The pressure transducer 22 is preferably located proximate the sample probe 24 to thus improve the signal to noise ratio of the pressure measurement. The sample probe 24 is controlled by a robot arm 23 to move to and/or from a cuvette 32 to aspirate or dispense in an automated assay system or to/from a tip stations 25 and test tube 27. In response to fluid flow through the pressure transducer 22 the transducer provides an electrical signal through a signal line 26 to a detector system 28. The detector circuit 28 receives input signals from the transducer 22 and provides output signals to the air source 12 and to a microprocessor based control system 33 via a microprocessor bus 30.

The detector system 28 detects the occurrence or non-occurrence of different events throughout an analyzer cycle automated analyzer system.

In response to the input signals from the transducer 22, the detector system 28 provides a plurality of functions to indicate by appropriate output signals when a distal end of the sample probe 24, typically having a pipette tip, physically contacts a fluid sample 31 disposed in tube 27 or cuvette 32 into which the sample probe 24 is lowered by arm 23.

Figure 2:
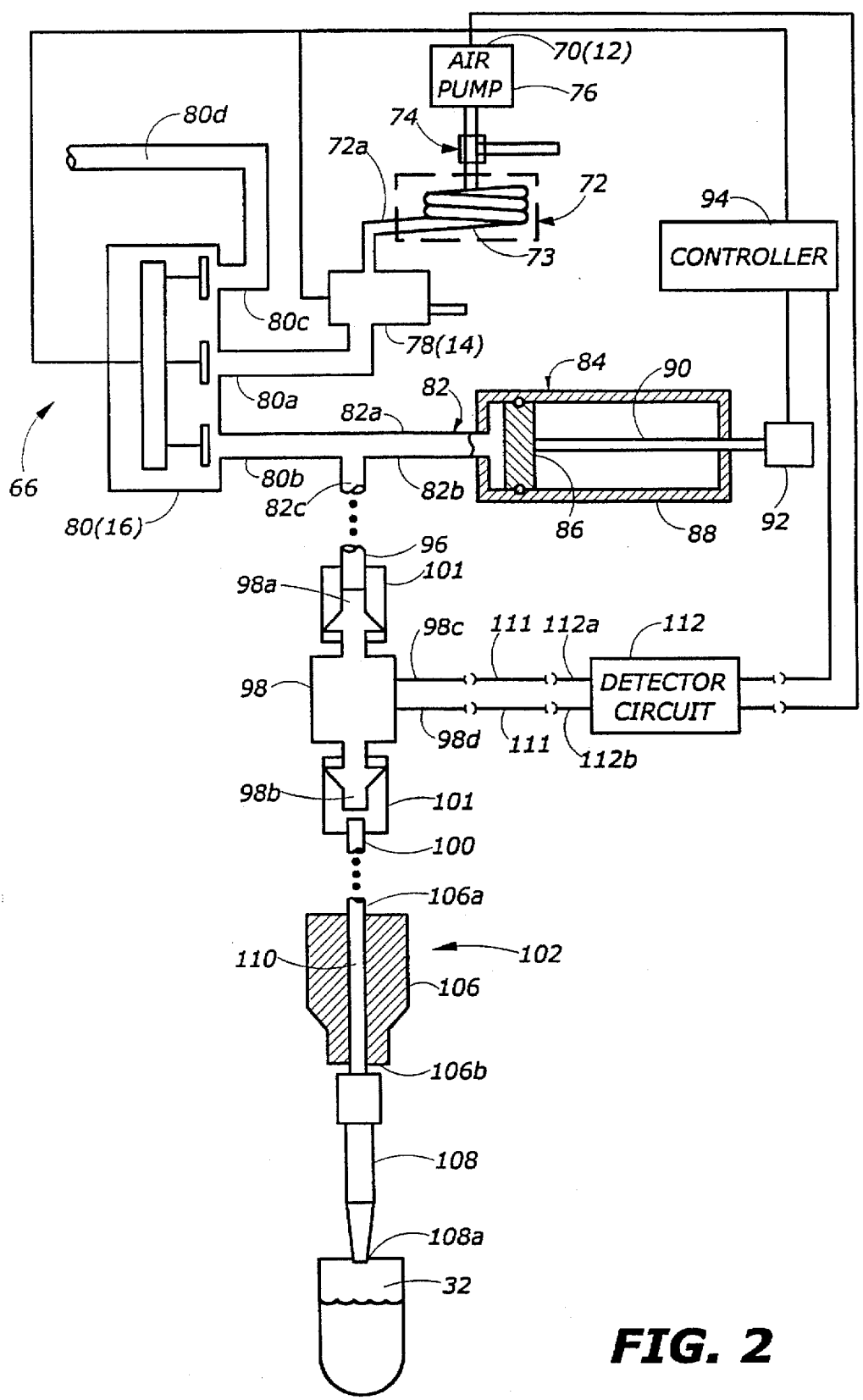
FIG. 2 is a diagrammatical view of an automated fluid sample aspiration/dispensation apparatus.

FIG. 2 shows in more detail the system of FIG. 1. As shown therein an aspirating and dispensing apparatus includes constant air source which here includes an air pump 70 coupled to an accumulator 72 having a vessel in which air provided from the air pump 70 is stored at a particular pressure such that a supply of air at a constant, low pressure is immediately available at an output port 72a of the accumulator. In this particular embodiment, the accumulator 72 is provided as a coil of tubing 73 which acts to regulate the pressure and variable flow rates and is diminished according to the needed slow regulation in pressure measurement.

A three port connecting member 74 disposed between the coil 73 and the air pump 70 has a first port coupled to the output port of the air pump 70 and a second port coupled to a first port of the coil 73. A third port of the connecting member 74 provides a vent port to which is coupled a vent tube 76.

To ensure proper operation of the aspirating and dispensing apparatus, the air pump 70 provides a relatively low air flow at the output port 72a of the accumulator 72. To provide such an air flow connecting member 24 vents a portion of the flow from air pump 70.

The vent tube 76 may preferably be provided as part of the coil 73 (e.g. provided on an inside portion the accumulator coil 73). The vent 76 establishes an upper pressure limit to which the pump 70 will be exposed even in the case of complete occlusion of the sample probe.

The accumulator 72 may also be implemented using other techniques well known to those of ordinary skill in the art.

The accumulator output port 72a is coupled through a bleed valve 14 to a common port 80a of pump valve 80 corresponding to pump valve 16. The pump valve 80 also includes a normally open port 80b to the sample probe and a normally closed port 80c to a vent 80d. The pump valve 80 is controlled by a controller 94.

The port 80b of pump valve 80 is coupled to a first port 82a of a three port connecting member 82. A second port 82b of the three port connecting member 82 is coupled to a diluter 84. The diluter 84 may be provided for example as a syringe pump in which the movement of a piston 86 in a first direction forces fluid from a housing 88 while movement of the piston 86 in a second opposite direction pulls fluid into the housing 88 through port 82b.

A shaft 90 couples the piston 86 to a linear stepper motor 92. In response to signals received from controller 94, the stepper rotor 92 drives the piston 86 in first and second opposite directions within the housing 88. In a preferred embodiment, the controller 94 is provided as a microprocessor based controller.

A third port 82c of the three port connecting member 82 is connected to a tube 96 having an inner diameter which fits the port 82c sealing the connection.

A pressure transducer 98 has a first port 98a coupled to a second end of the tube 96 and a second port 98b coupled to a first end of a typically resilient tube 100. A second end of the tube 100 is coupled to a first port of a sample probe 102. Thus the connecting element 82 and tubes 96, 100 and pressure transducer 98 provide a fluid path between the sample probe 102 and the pump valve 80 and diluter 84.

The pressure transducer 98 is here provided as a flow through pressure transducer of the type manufactured by the Micro Switch Division of Honeywell Corporation and identified as a 26PC Series pressure transducer and more particularly as part number 26PC BFG 6G. The sensitivity of the transducer 98 corresponds to about 10 mV/PSI of pressure difference. Other flow through pressure transducers having suitable fluid and electrical characteristics may also be used.

To facilitate connecting of the transducer ports 98a, 98b to the respective ones of the tubes 96, 100 with substantially different diameters, each of the ports 98a, 98b has coupled thereto a mating tube 101. The mating tubes 101 are provided from a relatively flexible material having a relatively high elasticity characteristic and a non-stretched diameter selected to accept the outside diameter of the tubes 96, 100 with a slight interference fit.

The sample probe 102 includes a probe body having a channel 110 between a first fluid port 106a to which the system tubing 100 is coupled and having a second fluid port 106b to which a sample probe tip 108 is coupled. In this particular embodiment, the sample probe tip 108 is provided as a disposable sample probe tip which is removably coupled to the sample probe body 106. It should be appreciated, however, that in some applications it may be desirable to provide the sample probe tip as a non-disposable plastic tip which is permanently secured to the sample probe body 106.

The tube 100 which couples the transducer 98 to the sample probe 102 is here provided having a length typically of about nine and one-half inches. It is desirable to minimize the distance between the sample probe 102 and the pressure transducer 98. In some applications, it may be desirable or even necessary to place the pressure transducer 98 closer than nine and one-half inches from the sample probe 102 and as close as possible to the sample probe 102.

In applications in which it is desirable to maximize sensitivity of the apparatus 66 to small changes in pressure, for example, it would be desirable to directly mate the transducer 98 to the sample probe 102. In practical applications, however, it is often not possible due the size of circuit components and available packaging space to achieve this goal. Thus, as trade-off, the pressure transducer 98 should be coupled to the sample probe 102 via a tube which minimizes the length of the fluid path between the transducer 98 and the sample probe 102.

For this purpose the pressure transducer 98 may be disposed on a printed circuit board (PCB) coupled to the sample probe 102 or as mentioned above, if space permits the pressure transducer may be directly disposed on the sample probe 102.

In this particular embodiment the flow through pressure transducer 98 has a pair of electrical terminals 98c, 98d one of which corresponds to a positive output terminal and one of which corresponds to a negative output terminal of the transducer 98. The transducer 98 provides a differential output voltage on the output terminals 98c, 98d representative of the pressure difference between the pressure in the sample probe tip and an ambient atmospheric pressure.

The transducer 98 is electrically coupled through lines 111 to a detector circuit 112 at a pair of input terminals 112a, 112b. The detector circuit 112 receives input signals from the pressure transducer 112 and provides at its output terminals output signals to controller 94 and to the air pump 70.

In operation, prior to aspirating a sample fluid from a tube 27 or cuvette 32, the vent port 80c of pump valve 80 is initially closed and the common and sample probe ports 80a, 80b are initially open. Also, the vent port of the bleed valve 78 is closed and the piston 86 is positioned so that no fluid is inside the housing 88. The air pump 70 is then turned on, forcing air through a fluid path which leads to the sample probe tip 108a. Thus air is forced out of the sample probe tip at a predetermined rate which creates a predetermined pressure measured by Pressure Transducer 98.

The sample probe 106 is moved toward a region in which fluid is expected to be contacted such as in the tube 27.

When the sample probe tip 108a initially contacts fluid, the tip 108a is occluded by the fluid. This results in the fluid conduit coupled between air pump 70 and the sample probe 108, including fluid lines 96, 100, being pressurized. The pressure transducer 98 senses the increased pressure level and provides a transducer signal to the detector circuit 112.

The detector circuit 112 then provides a control signal to the controller 94 which stops the sample probe from being lowered further or beyond a preset point into the fluid sample. The controller 94 provides control signals to open the vent port of the bleed valve 78 to thus de-pressurize the fluid path between the air pump 70 and sample probe 102 including the fluid path in which the pressure transducer 98 is disposed.

After the fluid lines have been de-pressurized, the controller 94 closes the vent port of the bleed valve 78. De-pressurizing the fluid path between the diluter 84 and the connecting member 82 prior to moving the piston 86 improves the ability of the system to accurately determine the aspirate and dispense fluid volumes. If the fluid path between diluter 84 and connecting member 82 were pressurized when the piston 86 began to move the diluter 84 would initially be forced to overcome the pressure built up in the fluid path. Thus, rather than aspirating fluid in response to movement of piston 86, pressure in the fluid path between the diluter 84 and sample probe 102 would be equalized with the pressure in the diluter, otherwise it is relatively difficult to precisely determine the amount of fluid which was drawn in by the diluter 84.

However, by opening and then closing the bleed valve 78 the pressure in the fluid line is set to atmospheric pressure. Thus, fluid can be immediately drawn into the sample probe tip 108 in response to operation of the diluter 84.

The apparatus also detects leaks in the fluid paths. To detect leaks, the sample probe tip 108a is completely occluded and the tubing is pressurized by turning on the pump 70. The probe tip 108a is occluded and the pump 70 is left on. The pressure in the fluid path between sample probe 102 and connecting member 82 is thus allowed to rise to a predetermined limit established during a calibration routine. If no leaks exist, then the pressure will rise to substantially the same calibration level each time the sample probe is occluded. If a leak exists, however, the pressure will not rise to substantially the same level each time.

For each system a calibration routine will be performed whereby the tip is occluded and the pressure to which fluid in the fluid paths rise is determined. The tip 108a may be occluded, for example, by placing a calibration tip onto the sample probe body 106. Such a calibration tip would be provided having an opening in one end thereof to be attached to the sample probe port 106b and no opening in the second end thereof.

The system controller 94 would then perform a sample probe calibration routine to establish a threshold pressure and voltage.

Figure 3:
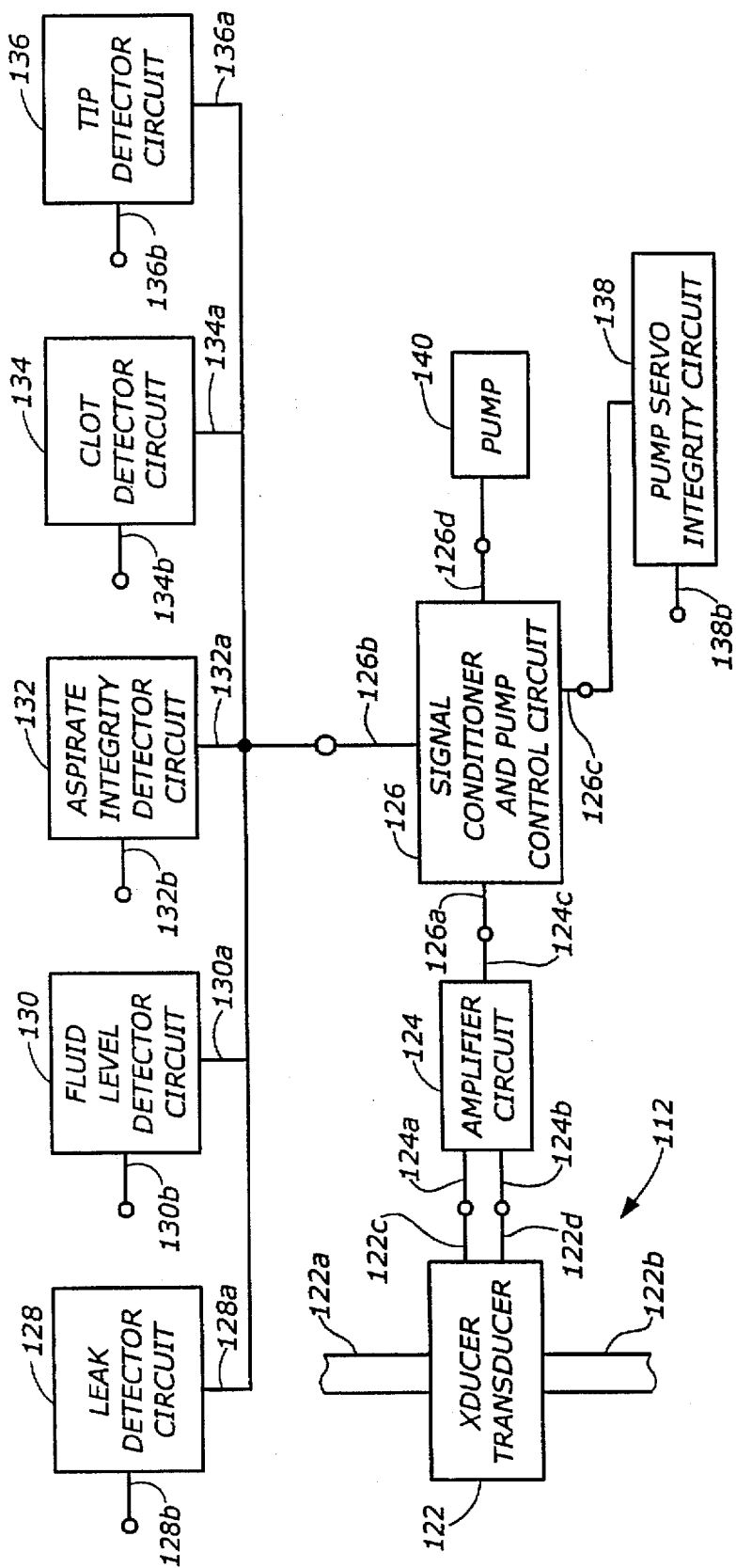
FIG. 3 is a block diagram of a detector system.

Referring now to FIG. 3, detector circuit 112 is shown to include a fluid pressure transducer 122 (corresponding to transducer 98 and 22) having a pair of fluid ports 122a, 122b and a pair of electrical signal terminals 122c, 122d on which a differential electrical signal is coupled to an amplifier circuit 124. The transducer 122 detects pressure changes which result in the fluid path due to the occurrence of particular events. For example, the transducer 122 senses pressure changes which result from a number of events including, but not limited to some or all of the following: (a) fluid leaks in a fluid path; (b) contact between a sample probe tip and a surface of a fluid; (c) aspiration of air through a sample probe; (d) obstruction of a sample probe tip; and (e) attachment and detachment of a sample tip to a sample probe.

In response to each of these events, the flow through pressure transducer 122 provides a corresponding differential voltage signal to an amplifier circuit 124 at input terminals 124a, 124b. The amplifier circuit 124 receives the differential signal fed thereto from the pressure transducer 122 and provides an amplified single ended output signal at an output terminal 124c thereof. The amplified output signal is fed to an input terminal 126a of a signal conditioner and pump control circuit 126.

A plurality of event detector circuits 128, 130, 132, 134 and 136 are coupled to an output terminal 126b of the signal conditioner and pump control circuit 126 to receive a pressure signal and a pump servo integrity circuit 138 is coupled to an output terminal 126c of signal conditioner and pump control circuit 126. While each of the circuits 128, 130, 132, 134 and 136 will be described further below in general each of the circuits 128, 130, 132, 134 and 136 receives an input signal from signal conditioner and pump control circuit 126 at respective input terminals 128a, 130a, 132a, 134a and 136a thereof and compares the signal level of the input signal to one or more threshold signal levels internally generated. Each of the circuits 128, 130, 132, 134 and 136 may be provided having different threshold signal levels. Circuit 126 may be software implemented or otherwise as may be effective In response to the input signal having a signal level either greater or less than the threshold signal levels, each of the circuits 128, 130, 132, 134, 136, and 138 provide representative output signals at the output terminal thereof. Each of the output terminals 128b, 130b, 132b, 134b, 136b, and 138b are coupled to controller 94 described above in conjunction with FIG. 2.

The output signals indicate whether or not a particular event occurred or the status of the aspirate-dispense apparatus. It should be noted that each of the circuits 128, 130, 132, 134, 136 and 138 and 126 may be implemented via a programmed microprocessor or alternatively may be implemented via comparator circuits.

An output terminal 126d of the signal conditioner and pump control circuit 126 is coupled to an air pump 140 corresponds to pump 70.

The leak detector circuit 128 receives the signal on line 126b and detects whether any leaks exist in the fluid paths of the apparatus (FIG. 2). When operating in a leak detection mode the controller 94 (FIG. 2) pressurizes the fluid paths in the apparatus. Leak detector circuit 128 measures the signal level of the signal on line 126b and in response to the signal level detector circuit 128 provides a signal to controller 94. The signal level of the line 128b signal indicates to controller 94 whether or not a leak exists in the fluid paths of apparatus 66.

Fluid level detector circuit 130 detects when the distal end 108a of the sample probe tip 108 physically contacts and is inserted into a sample fluid.

Aspirate integrity detect circuit 132 detects whether or not pump valve 80 is operating correctly. After a tip is placed on the sample probe, the sample probe port 80b of pump valve 80 (FIG. 2) is closed and air is aspirated. This should result in a pressure change to a predetermined level. If there is a leak in the tubing or the sample probe port 80b did not close, then the pressure change will not reach the proper level. Thus the aspirate integrity detect circuit 132 indicates whether or not the pump valve 80 has worked correctly.

Clot detector circuit 134 detects whether or not the sample probe tip 108 was occluded during aspirate and dispense operations. In those applications where probe tip 108 is provided as a plastic disposable probe tip, tip detector circuit 136 detects when the probe tip is coupled to and decoupled from the sample probe body 106 based on a change in pressure to predetermined levels in each case.

Pump servo integrity circuit 138 monitors the voltage signal used to servo the air pump 140 and determines whether or not an appropriate servo voltage is being applied to the pump 140. An incorrect voltage would indicate an error in condition such as a blocked flow path.

By examining detector signals provided from detector circuits 128, 130, 132, 134, 136 and 138, a number of failures in the aspirate and dispense apparatus of FIG. 2 can be detected. For example, a failed pressure transducer, a failed air pump or a bleed valve stuck in the open position (i.e. always bleeding) may be detected by examining signals on lines 130b, 136b and 138b. A bleed valve stuck in the closed position (i.e. never bleeding) may be detected by examining the line 130b signal.

Similarly, the 132b signal may be examined to detect if the sample probe port of the pump valve is stuck in the open position so as to continuously provide air from the air pump 70 (FIG. 2) to the sample probe 102. A pump valve stuck in the closed position such that the pump valve fails to provide air to the sample probe 102 may be detected by examining the 130b and 138b signals.

A leak in the tubing large enough to affect dispense performance or the level sense operation may be detected by examining the line 138b, 132b and 128b signals.

It should be noted that each of the event detector circuits 128, 130, 132, 134, 136 and 138 compares the respective input signal fed thereto to internally generated threshold voltage levels to determine the occurrence or non-occurrence of particular events. In response to the compare operations, each of the event detector circuits 128, 130, 132, 134, 136 and 138 provides an appropriate output signal to controller 94.

Figure 4:
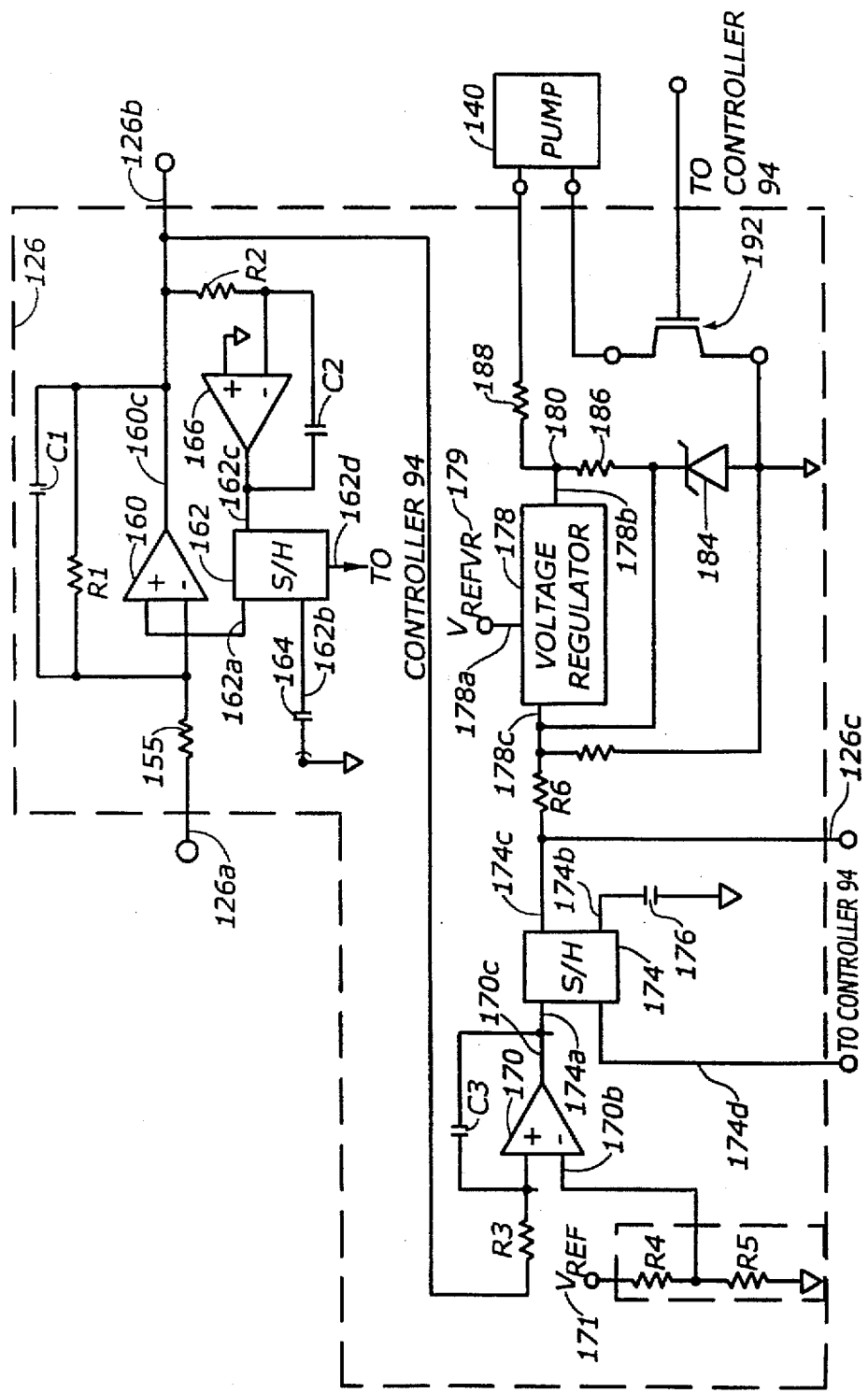
FIG. 4 is a schematic diagram of detector circuits for various functions.

Referring now to FIG. 4, the details of the signal conditioner and pump control circuit 126 are shown.

The input to the signal conditioner and pump control circuit is coupled through a resistor 155 to an inverting input of an inverting amplifier 160. The inverting amplifier 160 provides the line 126b signal to the detectors 128, 130, 132, 134 and 136.

A resistor R1 and capacitor C1 are coupled in a negative feed-back path as shown between the output terminal of the inverting amplifier 160 and the inverting input terminal of the amplifier 160. A non-inverting input of the inverting amplifier 160 is coupled to a first terminal 162a of a sample and hold circuit 162.

A charge storing capacitor 164 for the hold function is coupled between a second terminal 162b of the sample and hold circuit 162 and ground. A third terminal 162c of the sample and hold circuit 162 is coupled to an output terminal of a second inverting amplifier 166 and a fourth terminal 162d of the sample and hold circuit 162 is coupled to the system controller 94.

The non-inverting input of the second inverting amplifier 166 is coupled to ground and the inverting input of the amplifier 166 is coupled through a resistor R2 to the output terminal of the first inverting amplifier 160. A feedback capacitor C2 is coupled between the output and the inverting input of the amplifier 166.

The output terminal 160c of the first amplifier 160 is also coupled through a resistor R3 to an inverting input of a third inverting amplifier 170. The non-inverting input of the inverting amplifier 170 is coupled to a reference voltage 171 through a voltage divider network 172 having resistors R4, R5 selected in conjunction with the voltage level of the reference voltage 171 such that a predetermined threshold voltage is provided to the non-inverting input terminal 170b of the inverting amplifier 170.

A capacitor C3 is coupled between the output terminal and inverting input of amplifier 170.

The output terminal 170c of the third inverting amplifier 170 is coupled to a first terminal 174a of a sample and hold circuit 174. A charging capacitor 176 is connected between a second terminal 174b of the sample and hold circuit 174 and ground. A third terminal 174c of the sample and hold circuit 174 is coupled through a resistor R6 to an input terminal 178c of a voltage regulator circuit 178 and a fourth terminal 174d of the sample and hold circuit 174 is coupled to the system controller 94. The system controller provides a control signal to the sample and hold circuit causing it to operate in either a sample mode or a hold mode.

The voltage regulator 178 has a voltage input terminal 178a coupled to a reference voltage source 179. A voltage output terminal 178b of regulator 178 is coupled through a resistor 188 to control pump 140. A zener diode 184 is coupled between the input 178c and ground clamping the input to not exceed a predetermined voltage.

A resistor 186 is coupled between node 180 and the anode of the zener diode 184 as shown. A switch 192 is coupled between a second terminal of pump 140 (corresponding to air pump 70) and ground. In response to a first control signal from controller 94 the switch 192 is made conducting, activating the air pump 140.

The sample and hold circuit 162 establishes a reference or normalized voltage level for the signal on line 126b corresponding to a reference or normalized pressure level in the pressure transducer 122.

The sample and hold circuit 162 is placed in sample mode by the controller 94 in which it connects a signal path between the output of amplifier 166 and the non-inverting input of amplifier 160. Amplifier 166 provides an output signal to sample and hold input terminal 162c.

Amplifier 166 provides a bias signal at its output that is applied to the non-inverting input of amplifier 160 via sample and hold circuit 162 until the signal provided at the output of amplifier 160 is driven to a voltage level corresponding to ground. At this point controller 94 provides a second control signal to sample and hold terminal 162d which places the sample and hold circuit in the hold mode. The voltage level of the sample and hold circuit is thus setting a value which causes the line 126b output to be zero for what ever pressure is sensed. Thereafter the voltage level of the signal on line 126b is representative of relative pressure changes detected by the pressure transducer.

System operation:
(1) a system cycle begins with the sample probe 102 (FIG. 2) without a tip. A control signal from the controller 94 (FIG. 2) biases the switch 192 into its non conduction state thus decoupling the air pump 140 from ground and thereby turning off the air pump 140. With air pump 140 off, no pressure exists in the fluid path in which the flow through pressure transducer 122 is disposed. Thus, the pressure transducer 122 provides a differential output signal corresponding to zero pressure to the input terminals of the amplifier 124 (FIG. 3).

Also with the pump 140 turned off, the voltage regulator 178 and zener diode 184 maintain the voltage at line 178b at a set voltage level. Furthermore, the output terminal of amplifier 170 provides a voltage level corresponding to the rail voltage.

(2) The controller 94 then provides a control signal to the sample and hold circuit 162. In response to the control signal, the sample and hold circuit 162 drives output 126b to zero volts.

(3) The controller 94 then provides a control signal to turn the pump valve 80 on (FIG. 2) and also provides a second control signal to bias the switch 192 into its conduction state thereby turning on the air pump. When the pump is initially turned on the voltage across the pump is at a high voltage. When pump 140 is first turned on amplifier 170 servos the pump voltage so that line 126b is at the voltage at its noninverting input. Prior to the pump turn-on, the output of amplifier is at the positive rail driving current through resistor 176 and forcing line 178c to the zener voltage set by zener 184. This causes a rapid spinning of pump 140. Over time, amplifier 170 servos the loop resulting in its output falling as line 126b increases with the build up of the pressure signal from transducer 122. At a desired pressure voltage, the sample and hold circuit 174 is caused by controller 94 to hold that voltage for a cycle. Also, in response to the pump being turned on the pressure in the system fluid lines rises rapidly.

(4) After a period of typically 500 milli-seconds the controller 94 provides a control signal on line 176d to the control port of the second sample and hold circuit 174 thus placing the sample and hold circuit in the hold mode. The zeroing of output line 126b procedure of step "2" is repeated here as a very fast recalibration step.

(5) The controller 94 then measures the output of the integrity circuit 138 to determine if the signal is within a predetermined voltage range. If the signal has a voltage level outside a predetermined voltage range then an error signal is generated by the controller 94 and processing stops. If the signal has a voltage level within a predetermined voltage range then processing continues and the controller moves the sample probe 102 via robot arm 23 to a station 25 (FIG. 1) at which it may pick up a disposable probe tip.

(6) Line 126b is again zeroed as in step "2" and a fresh tip is placed on the probe. During placement of a probe tip on the probe body, the air in the line experiences a brief transient as the tip is inserted. Controller 94 examines the signal on line 136b from detector 136 to determine whether the signal corresponds to a preset level for a predetermined period of time to confirm tip placement. The pump filter is on and all values stay as set.

(7) The controller 94 turns off the pump valve 80. The air pump 140 remains running.

(8) Line 126b is zeroed again according to step "2"

(9) Once the tip is coupled to the sample probe body, the controller 94 engages the stepper motor 92 which draws the piston 86 into the cylinder 84. Since the tip has not yet been disposed in a fluid, this results in air being aspirated into the fluid paths through the disposable sample probe tip. After the aspiration is complete, the controller determines whether an error exists via the aspirate integrity detector circuit 130 (FIG. 3) as follows

(10) The controller 94 turns the pump valve 80 on thus supplying air flow to the sample probe 102. The controller 94 then zeros line 126b.

(11) The controller 94 moves the sample probe via robot arm 23 to a position in which the sample probe can access a sample tube 27 holding a fluid sample.

(12) The sample probe is lowered in the direction of the fluid tube 27. Once the disposable probe tip reaches the fluid, the pressure transducer 122 senses a change in pressure and provides a signal to the detector circuit 112. In response to the signal provided thereto from the pressure transducer 122, the detector circuit 130 generates a signal on output 130b and provides the signal to the controller.

(13) While monitoring line 130b, the controller 94 moves the disposable tip into the fluid sample to a predetermined penetration depth selected to allow aspiration of the needed fluid.

(14) After the disposable tip is moved to the predetermined depth, the controller waits for a predetermined period of time, typically about 500 msec. and then examines the signal on line 128b provided by leak detect circuit 128 (FIG. 3) to determine if any leaks are present in the system.

(15) The controller 94 provides control signals to turn on the bleed valve and turn off the air pump as described above to normalize the fluid line in preparation for aspirating fluid.

(16) The controller 95 then turns off the pump valve 80 and

(17) engages the stepper motor 92 (FIG. 3) causing the diluter to aspirate fluid into the sample probe tip 108. The controller 94 also monitors the line 134b signal provided by clot detector circuit 134 to determine if the sample probe fluid path has been obstructed during the aspirate operation.

(18) If no clot detection occurs then the controller 94 moves the sample probe to a position in which a sample fluid may be dispensed into a cuvette 32.

(19) The controller 94 provides a control signal causing the stepper motor to dispense the sample fluid into the cuvette 32. The controller again examines the line 134b signal to determine if the sample probe fluid path has been obstructed during the dispense operation.

(20) After the dispense operation is complete the controller 94 moves the probe body to eject the disposable tip. The signal on line 136b provided by tip detector circuit 136 (FIG. 3) should be present a few msec. thereby indicating that the disposable tip is removed from the sample probe body.

A leak is detected by leak detection circuit 128 (FIG. 3) in the following manner. As described above in conjunction with FIG. 4, the disposable tip of the sample probe is moved toward the fluid sample with the air pump on thus allowing the detection of the fluid sample level. Once the disposable tip is disposed in the fluid, the air pump remains on thereby letting pressure build up in the fluid lines.

The air pump provides the air at a flow rate which does not allow the pressure to rise to a level which causes a bubble in the sample fluid. Rather, pressure in the sample probe and fluid path leading thereto builds to a static pressure. The pressure range of the static pressure will be known from a calibration step to be described below.

The predetermined static pressure level corresponds to an equalizing pressure. Ideally the pressure should build up to the same value each time although in practice it is recognized that this will not be the case. However, if a hole or fluid leak exists in the fluid path then the pressure will not rise to the predetermined level and thus the line 126b signal will not reach a comparison threshold voltage level established in circuit 128. The circuit 128 will thus provide an output signal on line 128b which indicates that the threshold has not been reached and that a leak exists in the fluid path.

The static pressure and thus the threshold needed in circuit 128 will not be the same for every instrument. Rather it is a function of the tubing length, tubing diameters, and mechanical tolerances of each of the system components, etc. . . . Thus, a calibration step is used to set the threshold.

To calibrate the system, steps 1–5 are repeated as above. The sample probe is completely occluded such as by placing a calibration tip having a closed end on the probe body. This establishes a calibration voltage for the comparison threshold of circuit 128. The actual threshold voltage in circuit 128 is set a small voltage below that to insure that the voltage on line 126b exceeds the threshold where leaks are not present and the output 128b changes to reflect that.

The level sense detect circuit 130 responds to the line 126b signal and compares it to an internal reference. The output on line 130b is high until the disposable tip contacts a sample fluid. Then, with the air pump continuing to provide an air flow resulting in the pressure transducer 122 causing a signal rise on line 126b above the threshold voltage the signal on line 130b drops typically to about zero volts, thus indicating that physical contact between the sample probe and the sample fluid has occurred.

The aspirate integrity circuit 132 receives the signal on line 126b and if it is below a threshold voltage level established internally provides an output signal on line 132b having a high voltage (typically 5 volts). Once the signal level on line 126b reaches the threshold voltage, the circuit 132b provides on line 182b a low voltage (typically zero).

During an aspiration operation, the vent port of the pump valve is opened and the sample probe port of the pump valve should be closed to thus isolate the bleed valve, the coil and air pump from the diluter and pressure transducer. However, it is not possible to determine whether the pump valve operated correctly. Thus with the sample probe port of the pump value closed, air is aspirated through the sample probe. This should result in a pressure change in the fluid path in which the transducer is disposed.

If a leak exists in the pump valve, however, the pressure generated due to the aspirate operation will not rise to the proper threshold level for circuit 132. Consequently the pressure transducer 122 would provide a signal having an amplitude insufficient to reach the threshold voltage. The circuit 132 thus provides at the output terminal 132b a signal having a voltage level indicating that a leak in the pump valve was detected during an aspirate operation.

The clot detection circuit 134 has a dual comparison function with a pair of threshold levels set to detect whether the voltage level of the signal on line 126b falls within a predetermined voltage range between them. This is because the pressure transducer 122 (FIG. 3) measures different pressure levels during aspirate and dispense operations. For example, when the diluter piston stops after being moved during an aspirate operation, the pressure measured by the transducer should drop below a predetermined threshold voltage. If the pressure transducer fails to indicate such a pressure drop then the voltage level of the line 126b signal would likewise not change, thus indicating that the sample probe tip was occluded.

Similarly, during a dispense operation the pressure should stay above a predetermined threshold voltage. If the pressure transducer senses a pressure drop or rise during a dispense operation, then the voltage level of the line 126b signal would likewise change to a level outside the predetermined threshold voltage range thus indicating that the sample probe tip was occluded during the dispense operation.

The clot detection circuit may also be of the type described in co-pending patent application Ser. No. 08/499, 820 filed Jul. 10, 1995 (CCD-192XX—VOLUME DETECTION APPARATUS AND METHOD) assigned to the assignee of the present invention and incorporated herein by reference The pump servo integrity circuit 138 with input terminal is coupled to an output terminal, line 126c, of the sample and hold circuit 174 (FIG. 4). If this air pump servo voltage signal is not within a predetermined range, then the pump servo integrity circuit 138 provides an output signal so indicating at output terminal 138b. This signal is only examined by the controller 94 when setting the pump voltage.

Two threshold voltages are provided in circuit 138 respectively set at opposite voltage extremes. The threshold voltage levels are selected such that if the line 126c signal level exceeds these threshold levels, it indicates that the pump control circuit is unable to servo the pump in the desired manner. Thus when the line 126c signal is between these thresholds, the line 138c output voltage level is high. When the line 126c signal is outside the threshold voltage range the output signal is about zero volts.

It should be noted, that in some embodiments, it may be preferable to detect the signal level of the line 126b signal rather than the line 126c signal in which case the threshold voltage levels would be set differently.

The tip detection circuit 136 has a pair of threshold levels set internally at +/−low voltages defining a range about zero for the line 126b signal level above which the line 126b signal goes upon tip installation and below which line 126b goes on tip removal.

Inside this range, the output 136b is high; outside the range the output is low.

When a disposable sample tip is placed on the sample probe body, the voltage level of the line 126b signal will rapidly rise. The controller 94 examines the signal level of line 136b at the output terminal of the tip detection circuit. The controller 94 detects the signal level of the line 136b signal and verifies that the signal remains high for a predetermined time period, typically about 10 msec. Then there exists a relatively high probability that a tip was in the tip holder and that a disposable tip was actually placed onto the probe body.

In a similar manner, when a disposable tip is removed from the probe body, a pressure change occurs and is detected by the pressure transducer. The pressure transducer provides a corresponding output signal having a voltage transient below the range which is detected. In the event that a tip is not removed, the controller 94 detects the line 136b signal staying in range and acts to prevent a new tip from being disposed over an old tip that was not removed.

Having shown the preferred embodiment, those skilled in the art will realize many variations are possible which will still be within the scope and spirit of the claimed invention. Therefore, it is the intention to limit the invention only as indicated by the scope of the claims.

What is claimed is:

1. An apparatus for aspirating and dispensing a sample fluid comprises:
    a constant air source having an output port;
    a pump valve having a first port coupled to the output port of said constant air source, a sample probe port and a vent port;
    a connecting member having a first port coupled to the sample probe port of said pump valve, a second port and a third port;
    a diluter having an output port coupled to the second port of said connecting member;
    a flow through pressure transducer having a first port coupled to the third port of said connecting member, a second port to provide a first pressure signal and a third port;
    a sample probe having a first port coupled to the third port of said flow through pressure transducer; a detector having a first port coupled to said second port of said transducer, said detector providing a second pressure signal; and
    a controller for said air source, pump valve, diluter and sample probe operating as a function of said second pressure signal.

2. The apparatus of claim 1 further comprising a bleed valve having a first port coupled to the output port of said constant air source and a second port coupled to the first port of said pump valve.

3. The apparatus of claim 2 further comprising an accumulator having a first port coupled to the output port of said air source and an output port coupled to the first port of said bleed valve.

4. The apparatus of claim 3 further comprising a connector having a first port coupled to the output port of said constant air source, a second port coupled to the first port of said accumulator and an output port coupled to a vent tube.

5. The apparatus of claim 4 wherein said flow through pressure transducer provides said first pressure signal on a pair of electrical output terminals comprising said second port and in response to pressure changes in a fluid path between said sample probe and said connecting member said flow through pressure transducer provides a differential output signal at the pair of electrical output terminals.

6. The apparatus of claim 1 wherein said controller comprises a microprocessor.

7. The apparatus of claim 1 wherein said detector provides said second pressure signal to said controller to indicate a plurality of conditions reflected by pressure in said transducer.

8. The apparatus of claim 1 wherein said detector comprises:
    an amplifier circuit having a first terminal coupled to said second port of said flow through pressure transducer and a second terminal;
    a signal conditioning circuit having a first terminal coupled to the second terminal of said amplifier circuit and a second terminal coupled to at least one of:
        (a) a leak detector circuit;
        (b) a fluid level detector circuit;
        (c) an aspirate integrity detector circuit;
        (d) a clot detection circuit;
        (e) a tip detector circuit; and
        (f) a pump servo integrity circuit
    each of which has a nominal state signal set therein by said signal conditioning circuit under operation of said controller.

9. The apparatus of claim 8 wherein said signal conditioning circuit comprises:
    a first inverting amplifier having a negative input terminal coupled to the first terminal of said signal conditioning circuit, a positive input terminal and an output terminal;
    a second inverting amplifier having a negative input terminal coupled to the output terminal of said first inverting amplifier, a positive input terminal coupled to ground and an output terminal;
    a sample and hold circuit having an input terminal coupled to the output terminal of said second inverting amplifier, an output terminal coupled to the positive input terminal of said first inverting amplifier and a control terminal; and said controller coupled to the control terminal of said sample and hold circuit.

10. An apparatus for aspirating and dispensing a sample fluid comprising:

a constant air source having an output port;

a bleed valve having a first port coupled to the output port of said constant air source and a second port;

a pump valve having a first port coupled to the second port of said bleed valve, a sample probe port and a vent port;

a connecting member having a first port coupled to the sample probe port of said pump valve, a second port and a third port;

a diluter having an output port coupled to the second port of said connecting member;

a flow through pressure transducer having a first port coupled to the third port of said connecting member a second port to provide a pressure signal, and a third port;

a sample probe having a first port coupled to the third port of said flow through pressure transducer; and a controller for said air source, bleed valve, pump valve, diluter and probe operating as a function of said pressure signal.

11. The apparatus of claim 10 further comprising a detector circuit coupled to the second port of said flow through pressure transducer.

12. The apparatus of claim 11 wherein said detector circuit comprises:

an amplifier circuit having a first terminal coupled to said flow through pressure transducer and a second terminal;

a signal conditioning circuit having a first terminal coupled to the second terminal of said amplifier circuit and a second terminal coupled to at least one of:
  (a) a leak detector circuit;
  (b) a fluid level detector circuit;
  (c) an aspirate integrity detector circuit;
  (d) a clot detection circuit; and
  (e) a tip detector circuit; and
  (f) a pump servo integrity circuit each of which having a nominal state signal level set therein by said signal conditioning circuit under operation of said controller.

13. The apparatus of claim 12 wherein said signal conditioning circuit comprises:

a first inverting amplifier having a negative input terminal coupled to the first terminal of said signal conditioning circuit, a positive input terminal and an output terminal;

a second inverting amplifier having a negative input terminal coupled to the output terminal of said first inverting amplifier, a positive input terminal coupled to ground and an output terminal;

a sample and hold circuit having an input terminal coupled to the output terminal of said second inverting amplifier, an output terminal coupled to the positive input terminal of said first inverting amplifier and a control terminal; and said controller coupled to the control terminal of said sample and hold circuit.

* * * * *